United States Patent
Langlois et al.

(10) Patent No.: US 11,150,179 B2
(45) Date of Patent: Oct. 19, 2021

(54) PHASING CORRECTION

(71) Applicant: Illumina, Inc., San Diego, CA (US)

(72) Inventors: Robert Langlois, San Diego, CA (US); Paul Belitz, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 922 days.

(21) Appl. No.: 15/863,241

(22) Filed: Jan. 5, 2018

(65) Prior Publication Data
US 2018/0195953 A1    Jul. 12, 2018

Related U.S. Application Data

(60) Provisional application No. 62/443,294, filed on Jan. 6, 2017.

(51) Int. Cl.
*H01J 40/14* (2006.01)
*G01N 21/25* (2006.01)
(Continued)

(52) U.S. Cl.
CPC ...... *G01N 21/253* (2013.01); *B01L 3/502715* (2013.01); *B01L 3/502761* (2013.01);
(Continued)

(58) Field of Classification Search
CPC .. G01N 21/253; G01N 15/1463; H04N 13/15; G16B 25/00; G16B 30/00;
(Continued)

(56) References Cited

U.S. PATENT DOCUMENTS 6,172,218 B1    1/2001  Brenner
6,210,891 B1    4/2001  Nyren et al.
(Continued)

FOREIGN PATENT DOCUMENTS

RU    2291197     1/2007
WO    91/06678    5/1991
(Continued)

OTHER PUBLICATIONS

Whiteford, "Swift: primary data analysis for the Illumine Solexa sequencing platform", vol. 25 No. 17, 2009, 2194-2199.
(Continued)

*Primary Examiner* — Georgia Y Epps
*Assistant Examiner* — Kevin Wyatt
(74) *Attorney, Agent, or Firm* — Weaver Austin Villeneuve & Sampson LLP

(57) ABSTRACT

Memory efficient methods determine corrected color values from image data acquired by a nucleic acid sequencer during a base calling cycle. Such methods may: (a) obtain an image of a substrate (e.g., a portion of a flow cell) including a plurality of sites where nucleic acid bases are read; (b) measure color values of the plurality of sites from the image of the substrate; (c) store the color values in a processor buffer of the sequencer's one or more processors; (d) retrieve partially phase-corrected color values of the plurality of sites, where the partially phase-corrected color values were stored in the sequencer's memory during an immediately preceding base calling cycle; (e) determine a prephasing correction; and (f) determine the corrected color values. In various implementations, these operations are all performed during a single base calling cycle. In certain embodiments, the methods additionally include using the corrected color values to make base calls for the plurality of sites. Sequencers may be designed or configured to implement such methods.

22 Claims, 11 Drawing Sheets

(51) Int. Cl.

| | |
|---|---|
| *C12Q 1/6874* | (2018.01) |
| *C12N 15/10* | (2006.01) |
| *G01J 3/02* | (2006.01) |
| *C12Q 1/6855* | (2018.01) |
| *C12Q 1/6806* | (2018.01) |
| *B01L 3/00* | (2006.01) |
| *G16B 30/00* | (2019.01) |
| *G16B 25/00* | (2019.01) |
| *C12Q 1/6869* | (2018.01) |
| *H04N 13/15* | (2018.01) |
| *G01N 15/14* | (2006.01) |
| *G16B 30/10* | (2019.01) |
| *G01N 21/05* | (2006.01) |
| *G01N 21/64* | (2006.01) |
| *G06F 5/00* | (2006.01) |

(52) U.S. Cl.
CPC ....... *C12N 15/1068* (2013.01); *C12Q 1/6806* (2013.01); *C12Q 1/6855* (2013.01); *C12Q 1/6869* (2013.01); *C12Q 1/6874* (2013.01); *G01J 3/0267* (2013.01); *G01N 15/1463* (2013.01); *G16B 25/00* (2019.02); *G16B 30/00* (2019.02); *G16B 30/10* (2019.02); *H04N 13/15* (2018.05); *G01N 21/6454* (2013.01); *G01N 21/6486* (2013.01); *G01N 2021/058* (2013.01); *G06F 5/00* (2013.01); *G06F 2201/805* (2013.01)

(58) Field of Classification Search
CPC ......... B01L 3/502715; B01L 3/502761; C12N 15/1068; C12Q 1/6806; C12Q 1/6855; C12Q 1/6869; C12Q 1/6874; G01J 3/0267
USPC ....................................................... 250/226
See application file for complete search history.

(56) References Cited

U.S. PATENT DOCUMENTS

| | | |
|---|---|---|
| 6,258,568 B1 | 7/2001 | Nyren |
| 6,274,320 B1 | 8/2001 | Rothberg et al. |
| 6,306,597 B1 | 10/2001 | Macevicz |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,427,673 B2 | 9/2008 | Balasubramanian et al. |
| 8,241,573 B2 | 8/2012 | Banerjee et al. |
| 8,951,781 B2 | 2/2015 | Reed et al. |
| 8,965,076 B2 | 2/2015 | Garcia et al. |
| 9,193,996 B2 | 11/2015 | Buermann et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr Ost et al. |
| 2007/0166705 A1 | 7/2007 | Milton et al. |
| 2008/0108082 A1 | 5/2008 | Rank et al. |
| 2009/0026082 A1 | 1/2009 | Rothberg et al. |
| 2009/0127589 A1 | 5/2009 | Rothberg et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg |
| 2012/0020537 A1 | 1/2012 | Garcia et al. |
| 2012/0270305 A1 | 10/2012 | Reed et al. |
| 2013/0079232 A1 | 3/2013 | Kain |
| 2013/0260372 A1 | 10/2013 | Buermann et al. |
| 2013/0316918 A1 | 11/2013 | Jiang |
| 2013/0345066 A1* | 12/2013 | Brinza ................. C12Q 1/6874 506/2 |
| 2014/0051584 A1* | 2/2014 | Davey .................. C12Q 1/6874 506/2 |
| 2015/0100247 A1* | 4/2015 | Koller ...................... G16B 5/00 702/20 |
| 2019/0218599 A1* | 7/2019 | Hubbell ............... C12Q 1/6874 |

FOREIGN PATENT DOCUMENTS

| | | |
|---|---|---|
| WO | 2004/018497 | 3/2004 |
| WO | 2005065814 A1 | 7/2005 |
| WO | 2006/064199 | 6/2006 |
| WO | 2007/010251 | 1/2007 |
| WO | 2007123744 A2 | 11/2007 |
| WO | 2015084985 A2 | 6/2015 |

OTHER PUBLICATIONS

Cockroft, et al., "A single-molecule nanpore device detects DNA polymerase activity with single-nucleotide resolution", J. Am. Chem. Soc, 130(3), Jan. 23, 2008, 818-820.

Deamer, et al., "Characterization of nucleic acids by nanopore analysis", ACC Chem Res, 35(10), 2002, 817-825.

Deamer, et al., "Nanopores and nucleic acids: prospects for ultrarapid sequencing", Trends Biotechnol, 18(4), 2000, 147-151.

Healy, Ken, "Nanopore-based single-molecule DNA analysis", Nanomed. 2(4), 2007, 459-481.

Korlach, et al., "Selective aluminum passivation for targeted immobilization of single DNA polymerase molecules in zero-mode waveguide nanostructures", PNAS, vol. 105 No. 4, 2008, 1176-1181.

Levene, et al., "Zero-Mode Waveguides for Single-Molecule Analysis at high concentrations", Science 299, 2003, 682-686.

Li, et al., "DNA molecules and configurations in a solid-state nanopore microscope", Nature Mater, 2(9), 2003, 611-615.

Lundquist, et al., "Parallel confocal detection of single molecules in real time", Opt. Lett. 33(9), 2008, 1026-1028.

Metzker, et al., "Emerging technologies in DNA sequencing", Genome Research, 15, 2005, 1767-1776.

Ronaghi, M et al., "A Sequencing Method Based on Real-Time Phyrophosphate", Science. Jul. 17, 1998; 281 (5375):363-365 USE, Jul. 17, 1998, 363-365.

Ronaghi, M et al., "Real-time DNA sequencing using detection of pyrophosphate release", Anal. Biochem. Nov. 1, 1996; 242 (1):84-9, Nov. 1, 1996, 84-89.

Ronaghi, Mostafa , "Pyrosequencing sheds light on DNA sequencing", Genome Res, 11(1), 2001, 3-11.

Ruparel, et al., "Design and synthesis of a 3'-O-allyl photocleavable fluorescent nucleotide as a reversible terminator for DNA sequencing by synthesis", PNAS, 102, 2005, 5932-5937.

Soni, et al., "Progress toward Ultrafast DNA Sequencing Using Solid-State Nanopores", Clin Chem, 53(11), 2007, 1996-2001.

International Search Report and Written Opinion dated May 4, 2018, in PCT/US2018/012580.

Russian Office Action dated May 27, 2021, in Appl. No. 2019122320 (English translation only).

* cited by examiner

| Cluster Number | 1 | 2 | 3 | 4 | 5 | 6 | 7 | 8 | 9 | 10 | 11 | 12 |
|---|---|---|---|---|---|---|---|---|---|---|---|---|
| Color Value (Channel 1) | 468 | 695 | 1255 | 521 | 753 | 1452 | 1355 | 1255 | 598 | 720 | 1193 | 422 |
| Color Value (Channel 2) | 1321 | 1466 | 1326 | 498 | 463 | 1384 | 632 | 558 | 452 | 1467 | 1369 | 1278 |

Figure 4

| | Density (K/mm2) | Clusters PF (%) | Cycles Err Rated | Aligned (%) | Error Rate (%) |
|---|---|---|---|---|---|
| Baseline | 206 +/- 0 | 81.32 +/- 0.69 | 150 | 1.43 +/- 0.01 | 1.38 +/- 0.00 |
| New | 206 +/- 0 | 81.80 +/- 0.00 | 150 | 1.42 +/- 0.00 | 1.41 +/- 0.00 |

| | Tiles | Density (K/mm2) | Clusters PF (%) | Aligned (%) | Error Rate (%) |
|---|---|---|---|---|---|
| baseline | 1 | 3815 +/- 0 | 65.39 +/- 0.00 | 1.43 +/- 0.00 | 1.89 +/- 0.00 |
| new | 1 | 3815 +/- 0 | 65.39 +/- 0.00 | 1.43 +/- 0.00 | 1.95 +/- 0.00 |

Figure 11

PHASING CORRECTION

CROSS-REFERENCE TO RELATED APPLICATIONS

This application claims the benefits of U.S. Provisional Patent Application No. 62/443,294, filed Jan. 6, 2017, and entitled "PHASING CORRECTION," which is hereby incorporated by reference in its entirety and for all purposes.

BACKGROUND

The disclosure relates to sequencing nucleic acids. More specifically, the disclosure relates to systems and methods for real time sequencing with phasing corrections.

At a particular site on a flow cell or other substrate, multiple copies of a nucleic acid molecule, all having the same sequence (possibly with limited variations unintentionally introduced by sample processing), are analyzed together. Enough copies are used to ensure that sufficient signal is produced to permit reliable base calling. The collection of nucleic acid molecules at a site is called a cluster.

Phasing represents an unintended artifact that arises from sequencing multiple nucleic acid molecules within a cluster. Phasing is the rate at which signals such as fluorescence from single molecules within a cluster lose sync with each other. Often the term phasing is reserved for contaminating signal from some molecules that fall behind, and the term pre-phasing is used for contaminating signal from other molecules that go ahead. Together phasing and pre-phasing describe how well the sequencing apparatus and chemistry is performing.

SUMMARY

Certain aspects of this disclosure pertain to methods of determining corrected color values from image data acquired by a nucleic acid sequencer during a base calling cycle, where the sequencer includes an image acquisition system, one or more processors, and memory. Such methods may be characterized by the following operations: (a) obtaining an image of a substrate (e.g., a portion of a flow cell) including a plurality of sites where nucleic acid bases are read; (b) measuring color values of the plurality of sites from the image of the substrate; (c) storing the color values in a processor buffer of the sequencer's one or more processors; (d) retrieving partially phase-corrected color values of the plurality of sites, where the partially phase-corrected color values were stored in the sequencer's memory during an immediately preceding base calling cycle; (e) determining a prephasing correction; and (f) determining the corrected color values. In various implementations, these operations are all performed during a single base calling cycle. In certain embodiments, the methods additionally include using the corrected color values to make base calls for the plurality of sites.

During sequencing, the sites exhibit colors representing nucleic acid base types. The measured and stored color values may be intensity or other magnitude values at a particular wavelength or range of wavelengths. In some implementations, the color values are determined from only two channels of the sequencer. In some implementations, the color values are obtained from four channels of the sequencer. While this disclosure focuses on phasing correction of color signals, the concepts apply to other types of signals generated during sequencing clusters of nucleic acids having identical sequences. Examples of such other signals include radiation outside the visible spectrum, ion concentration, etc.

In certain embodiments, determining the corrected color values in (f) uses (i) the color values in the processor buffer, (ii) the partially phase corrected values stored during the immediately preceding cycle, and (iii) the prephasing correction. In certain embodiments, determining the pre-phasing correction in (e) uses (i) the partially phase-corrected color values stored during the immediately preceding base calling cycle, and (ii) the color values stored in the processor buffer.

In certain embodiments, the prephasing correction includes a weight. In such embodiments, the operation of determining the corrected color values may include multiplying the weight by the color values of the plurality of sites measured from the image of the substrate.

In certain implementations, the methods additionally include determining a phasing correction for the immediately succeeding base calling cycle. As an example, determining the phasing correction for the immediately succeeding base calling cycle includes analyzing (i) the partially phase-corrected color values stored in the sequencer's memory, and (ii) the color values stored in the processor buffer. In certain embodiments including determining a phasing correction for the immediately succeeding base calling cycle, the methods additionally include (i) producing partially phase-corrected color values for the immediately succeeding base calling cycle by applying the phasing correction to color values of the plurality of sites stored in the sequencer's memory; and (ii) storing the partially phase-corrected color values for the immediately succeeding base calling cycle in the sequencer's memory. In certain embodiments, producing the partially phase-corrected color values for the immediately succeeding base calling cycle additionally includes summing (i) the phasing corrected color values of the plurality of sites, and (ii) the color values of the plurality of sites from the image of the substrate measured in (b). In some implementations, storing the partially phase-corrected color values for the immediately succeeding base calling cycle stores the partially-corrected color values in tile buffers of the sequencer's memory.

In certain embodiments, the methods are performed in real time during acquisition of sequence reads by the nucleic acid sequencer. In certain embodiments, the nucleic acid sequencer sequences by synthesizing nucleic acids at the plurality of sites. In certain embodiments where the substrate includes a flow cell, the flow cell is logically divided into tiles, and each tile represents a region of the flow cell comprising a subset of sites, which subset is captured in a single image from the image acquisition system.

In some embodiments employing such systems, in operation (d) (retrieving partially phase-corrected color values of the plurality of sites), the partially phase-corrected color values were previously stored in tile buffers of the sequencer's memory, where the tile buffers are designated for storing data representing images of individual tiles on the substrate. In certain embodiments, the memory has a storage capacity of about 512 Gigabytes or less, or about 256 Gigabytes or less. In certain embodiments, for example, the memory has a storage capacity of less than twice the capacity required to store the data contained in the total number of tiles on two flow cells. In some embodiments, the processing described herein saves at least about 50 Gigabytes; in some embodiments it saves at least about 100 Gigabytes.

In some implementations, prior to operation (a) (obtaining an image of a substrate), the methods additionally include providing reagents to the flow cell and allowing the reagents to interact with sites to exhibit the colors representing nucleic acid base types during the base calling cycle. In such implementations, the method may additionally include, after operation (f) (determining the corrected color values): (i) providing fresh reagents to the flow cell and allowing the fresh reagents to interact with the sites to exhibit colors representing nucleic acid base types for a next base calling cycle; and (ii) repeating operations (a)-(e) for the next base calling cycle. Such methods may additionally include creating a first processor thread for performing operations (a)-(f) for the base calling cycle, and creating a second processor thread for performing operations (a)-(f) for the next base calling cycle. In certain embodiments, the methods additionally include allocating the processor buffer and a second processor buffer, where the second processor buffer is used to determine the corrected color values in (f).

Certain other aspects of the disclosure pertain to nucleic acid sequencers which may be characterized by the following elements: an image acquisition system; memory; and one or more processors designed or configured to: (a) obtain data representing an image of a substrate including a plurality of sites where nucleic acid bases are read (the sites exhibit, e.g., colors representing nucleic acid base types); (b) obtain color values of the plurality of sites from the image of the substrate; (c) store the color values in a processor buffer; (d) retrieve partially phase-corrected color values of the plurality of sites for a base calling cycle (the partially phase-corrected color values were stored in the sequencer's memory during an immediately preceding base calling cycle); (e) determine a prephasing correction; and ((f) determine corrected color values from, e.g., (i) the color values in the processor buffer, (ii) the partially phase corrected values stored during the immediately preceding cycle, and (iii) the prephasing correction.

The instructions or other configuration for determining a prephasing correction may include configuration for determining the prephasing correction from (i) the partially phase-corrected color values stored during the immediately preceding base calling cycle, and (ii) the color values stored in the processor buffer.

In certain embodiments, the memory is divided into a plurality of tile buffers, each designated for storing data representing a single image of a tile on the substrate. In certain embodiments, the memory has a storage capacity of less than about 550 Gigabytes (in some examples, this is less than twice the capacity required to store the data contained in the total number of tiles on two flow cells).

The processors may be configured to perform the recited operations in various ways such as receiving executable machine readable instructions. In some cases, the processors are programmed with firmware or custom processing cores such as digital signal processing cores. In various embodiments, the processor(s) are designed or configured to perform (and/or control) any or more of the method operations described above.

In some implementations, phasing correction features disclosed herein substantially reduce the cost of a sequencing instrument by more efficiently utilizing memory (e.g., random access memory (RAM)). Some embodiments employ these phasing correction features in the context of real time analysis (RTA) on sequencing platforms These and other features of the disclosure will be presented in greater detail below, with reference to the associated drawings.

BRIEF DESCRIPTION OF THE DRAWINGS

FIG. 4 depicts a data array containing magnitude data for clusters in a tile or other imaged portion of a flow cell; the magnitude data may be light intensity values for each of two or more color channels.

FIG. 11 presents comparative data for phasing correction methods, one using a reduced main memory algorithm.

DETAILED DESCRIPTION

Definitions

Figure 1:
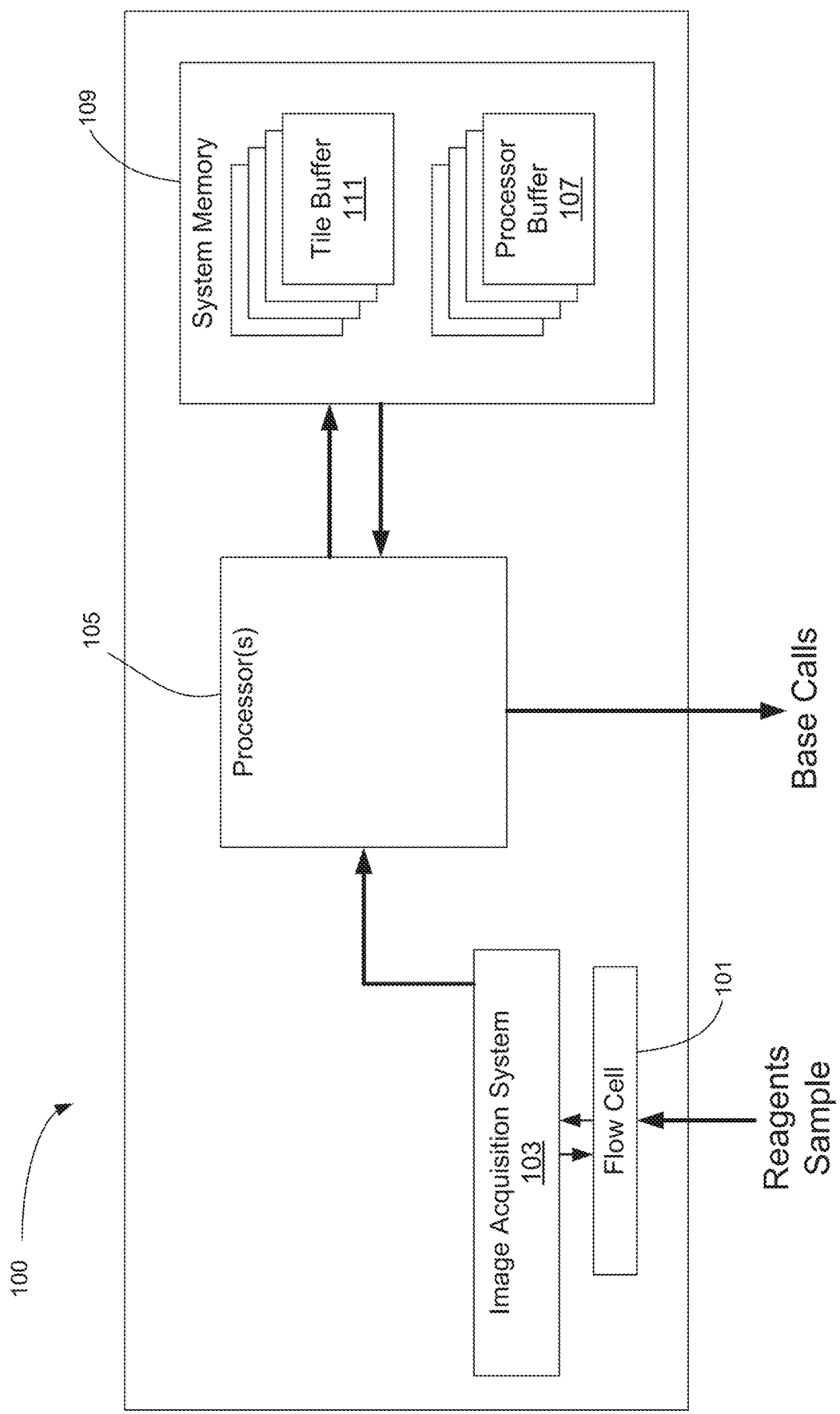
FIG. 1 is a block diagram of a sequencer with hardware for real time analysis of image data taken from nucleic acid clusters.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the specification as a whole. It is to be understood that this disclosure is not limited to the particular methodology, protocols, and reagents described, as these may vary, depending upon the context they are used by those of skill in the art.

As used herein, the singular terms "a," "an," and "the" include the plural reference unless the context clearly indicates otherwise. The term "plurality" refers to more than one element. For example, the term is used herein in reference to a number of reads to produce phased island using the methods disclosed herein.

The term "portion" is used herein in reference to the amount of sequence information of genome, chromosome, or haplotype in a biological sample that in sum amount to less than the sequence information of one complete genome, one complete chromosome, or one complete haplotype, as apparent from context.

The term "sample" herein refers to a sample, typically derived from a biological fluid, cell, tissue, organ, or organism containing a nucleic acid or a mixture of nucleic acids containing at least one nucleic acid sequence that is to be sequenced. Such samples include, but are not limited to sputum/oral fluid, amniotic fluid, cerebrospinal fluid, blood, a blood fraction (e.g., serum or plasma), fine needle biopsy samples (e.g., surgical biopsy, fine needle biopsy, etc.), urine, saliva, semen, sweat, tears, peritoneal fluid, pleural fluid, lavage fluid tissue explant, organ culture and any other tissue or cell preparation, or fraction or derivative thereof or isolated therefrom.

Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules. The term "polynucleotide" includes, without limitation, single- and double-stranded polynucleotide.

Single stranded polynucleotide molecules can have originated in single-stranded form, as DNA or RNA or have originated in double-stranded DNA (dsDNA) form (e.g. genomic DNA segments, PCR and amplification products and the like). Thus a single stranded polynucleotide may be the sense or antisense strand of a polynucleotide duplex. Methods of preparation of single stranded polynucleotide molecules suitable for use in the described methods using standard techniques are well known in the art. The precise sequence of the primary polynucleotide molecules is generally not material to the disclosed embodiments and may be known or unknown. The single stranded polynucleotide molecules can represent genomic DNA molecules (e.g., human genomic DNA) including both intron and exon sequences (coding sequence), as well as non-coding regulatory sequences such as promoter and enhancer sequences.

The nucleic acid described herein can be of any length suitable for use in the provided methods. For example, the target nucleic acids can be at least 10, at least 20, at least 30, at least 40, at least 50, at least 75, at least 100, at least 150, at least 200, at least 250, at least 500, or at least 1000 kb in length or longer.

In the context of a flow cell or other substrate for sequencing, the term "site" refers to small region where sequencing takes place. In many embodiments, a site contains multiple, typically numerous, copies of a single nucleic acid sequence from which sequencing data is obtained. The sequence data obtained from a site may be a "read."

The term "polymorphism" or "genetic polymorphism" is used herein in reference to the occurrence in the same population of two or more alleles at one genetic locus. Various forms of polymorphism include single nucleotide polymorphisms, tandem repeats, micro-deletions, insertions, indels, and other polymorphisms.

A "base call" is an assigned base (nucleotide type) to sequence data for a particular location in a polynucleotide sequence. A base call may be output by a sequencer for each position in nucleic acid being sequenced. A quality of the call is sometimes ascribed to a base call.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a physical property or a representation of that property. In some situations, a parameter numerically characterizes a quantitative data set and/or a numerical relationship between quantitative data sets. For example, the mean and variance of a standard distribution fit to a histogram are parameters.

The terms "threshold" herein refer to any number that is used as a cutoff to characterize a sample, a nucleic acid, or portion thereof (e.g., a read). The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. Sometimes they are chosen for a particular purpose (e.g., to balance sensitivity and selectivity).

Real time analysis refers to a process and system in which processing and data analysis are performed in the background of data acquisition during a DNA sequencing run. An example of a real time analysis system is described in U.S. Pat. No. 8,965,076, which is incorporated herein by reference in its entirety.

Context for Phasing

Sequence Apparatus

FIG. 1 shows a block diagram of some features of a typical nucleic acid sequencer 100 or a system including such sequencer. Notably, the system 100 includes a flow cell 101, and image acquisition system 103, one or more processors 105 with one or more buffers 107, and system memory (sometimes referred to as main memory) 109 including a plurality of tile buffers 111. Typically, system memory 109 is provided on device that is not part of an integrated circuit containing any of the one or more processor(s) 105. In certain embodiments, the system memory is volatile memory such as Random Access Memory or RAM, e.g., DRAM, a solid state hard drive, or a hard disk drive.

The flow cell and image acquisition system contain components designed or configured in accordance with principles understood in the field of nucleic acid sequencing, and they will not be described in detail herein. Suitable image analysis systems and associated flow cells are employed in nucleic acid sequencers such as the MiSeq and HiSeq series of sequencers available from Illumina, Inc. of San Diego, Calif. For additional information, see U.S. Pat. Nos. 8,241,573, 9,193,996, and 8,951,781, each of which is incorporated herein by reference in its entirety.

In general, nucleic acid sequences suitable for use with the disclosed methods provide rapid and efficient detection of a plurality of target nucleic acid in parallel. They can include fluidic components capable of delivering amplification reagents and/or sequencing reagents to one or more immobilized DNA fragments, the system including components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference in its entirety. As exemplified for flow cells, one or more of the fluidic components of an integrated system can be used for both an amplification method and for a detection method. For example, one or more of the fluidic components of an integrated system can be used for an amplification method and for the delivery of sequencing reagents in a sequencing method. Alternatively, an integrated system can include separate fluidic systems to carry out amplification methods and to carry out detection methods.

For purposes of this disclosure, it is sufficient to understand that the flow cell first receives and immobilizes or otherwise captures a nucleic acid sample which is to be sequenced and then exposed to various reagents associated with the sequencing process. In certain embodiments, the sequencing process is a sequence by synthesis process, although other sequencing technologies may be employed.

The image acquisition system 103 includes optical components such as fluorescence excitation components (e.g., a laser and associated mirrors and lenses) for illuminating sites on the flow cell where sequencing is taking place and image capture components for capturing images of fluorescence on portions of the flow cell having multiple sites. The data captured by the image acquisition system contains information suitable for determining which nucleotide is being read on any given site at any given sequencing cycle.

To allow for real-time analysis, the sequencer 100 typically includes onboard processors and memory that interpret and store image data from the image acquisition system 103. Examples of suitable processors for the sequencer include Intel's Xeon E5 class. Typically, the processor 105 includes multiple buffers 107 that temporarily store image data taken during a single image acquisition cycle. In the depicted embodiment, the processor buffers are allocated in the system memory. A given processor buffer may be associated with a particular processor thread created to analyze image data of a region of the flow cell during real time analysis. In certain embodiments, the image data analyzed by a thread is that of a single tile (described below), captured during a single image acquisition cycle. In certain embodiments, the buffer can store about 400 Gigabytes of data. As used herein, a thread is an ordered sequence of instructions that tells the processor what operations to execute. The instructions configure the processor using executable machine code selected from a specific machine language instruction set, or "native instructions," designed into the hardware processor.

The machine language instruction set, or native instruction set, is known to, and essentially built into, the hardware processor(s), or CPUs. This is the "language" by which the system and application software communicates with the hardware processors. Each native instruction is a discrete code that is recognized by the processing architecture and that can specify particular registers for arithmetic, addressing, or control functions; particular memory locations or offsets; and particular addressing modes used to interpret operands. More complex operations are built up by combining these simple native instructions, which are executed sequentially, or as otherwise directed by control flow instructions.

System memory 109 includes multiple tile buffers 111, each configured to store a portion of the image data acquired from the flow cell during a single image acquisition cycle. Tile buffers in this example are referred to as such because they are configured to hold a single tile's worth of image data. As explained more fully below, a tile is a region of a flow cell that can be captured in a single image taken during a single image acquisition cycle. Tile buffers 111 are intended to store image data over a longer period of time than processor buffers 107. In certain embodiments, tile buffers 111 store image data for at least two image acquisition cycles. While this application describes buffers that buffer data from a tile of a flow cell, the disclosed embodiments are not limited to buffers storing this amount of data. Unless otherwise stated or clear from context, references to "tile buffers" are understood to include any type of buffer that stores image data from a portion of a flow cell, which image data is processed as a unit as described herein.

To make base calls, the one or more processors 105 acts on data provided from system memory 109 and data stored in processor buffers 107. Typically, a single base call is made for a single site during a single image acquisition cycle.

As shown, the one or more processors 105 and the main memory 109 share data bi-directionally. Additionally, the one or more processors 105 receive image data from image acquisition system 103. In certain embodiments, image acquisition system 103 obtains data from flow cell 101 by exciting the sequencing sites on flow cell 101 and receiving optical signals from those sites. In certain embodiments, the signal received by image acquisition system 103 is a fluorescence signal created when system 103 illuminates flow cell 101 with light at appropriate wavelengths. In such embodiments, the fluorescence signal is provided as intensity values for a plurality of colors.

The concept of a cycle is used throughout this disclosure. A single sequencing cycle involves reading a single nucleotide from each of one or more sites captured on an image. The reading is referred to as making a base call. In various embodiments described herein, a single computational cycle—from the perspective of the processor(s) and memory—performs both base calling and image capture but for different nucleotides, with the base calling lagging image capture in the sequence of nucleotides being read or called. For example, in a single computational cycle, the one or more processors conduct base calling for a nucleotide in sequencing cycle n and concurrently conduct image capture for nucleotide in sequencing cycle n+1. Thus, in a single computational cycle, the sequencer (a) stores and processes unmodified image data for nucleotides in sequencing cycle n+1 and (b) makes a base call for nucleotides in sequencing cycle n. The use of the processor buffers and tile buffers in this cycle-by-cycle processing will be described in more detail below.

Phasing Generally

At a particular site on a flow cell or other substrate, multiple copies of a nucleic acid molecule, all having the same sequence (possibly with limited variations unintentionally introduced by sample processing), are analyzed together. Enough copies are used to ensure that sufficient signal is produced to permit reliable base calling. The collection of nucleic acid molecules at a site is called a cluster. In some cases, an unsequenced cluster contains only single stranded nucleic acid molecules.

Phasing represents an unintended artifact that arises from sequencing multiple nucleic acid molecules within a cluster. Phasing is the rate at which signals such as fluorescence from single molecules within a cluster lose sync with each other. Often the term phasing is reserved for contaminating signal from some molecules that fall behind, and the term pre-phasing is used for contaminating signal from other molecules that go ahead. Together phasing and pre-phasing describe how well the sequencing apparatus and chemistry is performing.

Low numbers are better. Values of 0.10/0.10 mean 0.10% of the molecules in a cluster are both falling behind and 0.10% are running ahead at each base calling cycle. In other words 0.20% of the true signal is lost each cycle and will therefore contribute to noise. Another example, 0.20/0.20 means that 0.4% of the true signal is lost per cycle, in which case after 250 cycles (without correction) the noise would be equal to the signal.

A real time analysis component of a sequencer may determine phasing and pre-phasing in order to apply the correct level of phasing correction as sequencing proceeds. This works by artificially pushing signal in or out of each sequencer channel based on base calls before or after the current cycle.

Previously, phasing and pre-phasing were estimated over a defined number of cycles (e.g., the first 12 cycles of each read) and then applied to all subsequent cycles. Some recent sequencers employ an algorithm called empirical phasing correction to optimize the phasing correction at every cycle by trying a range of corrections and selecting the one which results in the highest chastity (signal purity). While empirical phasing correction provides improved performance, it requires greater computational resources.

In conventional sequencers, each base has a unique fluorescent dye color; e.g., green to thymine, red for cytosine, blue for guanine, and yellow for adenine. To capture information for base calling, a four channel sequencer takes four images of a tile or other portion of a flow cell. Some sequencers now have only two channels, and therefore take only two images of the same portion of the flow cell. A two-channel sequencer uses a mix of dyes for each base and uses red and green filters for the two images. In an example of a two channel sequencer, clusters seen in red or green images are interpreted as C and T bases, respectively. Clusters observed in in both red and green images are flagged as A bases, while unlabeled clusters are identified as G bases.

Figure 2:
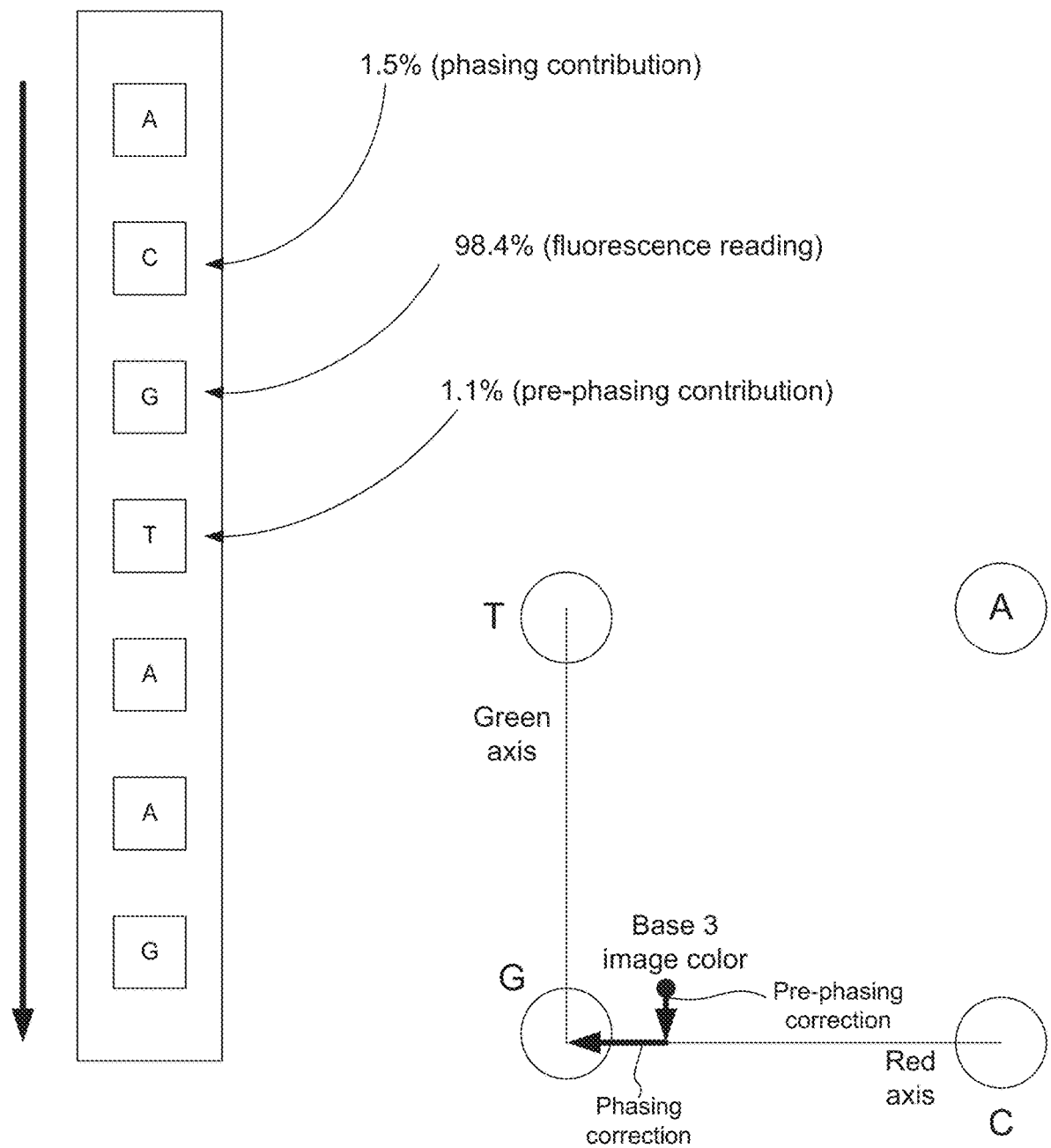
FIG. 2 is an illustration of two channel sequencing data used to illustrate the concepts of phasing and pre-phasing.

FIG. 2 illustrates phasing during sequencing of a nucleic cluster having the sequence . . . ACGTAAG . . . . As illustrated, the during the base calling cycle for the first G, 98.4% of the fluorescence signal originates from sequences currently generating signal for G, while 1.5% of the fluorescence signal originates from sequences currently producing signal for the prior base C, and 1.1% of the fluorescence signal originates from sequences currently producing signal for the next base T. The signal contribution for the prior base C is from phasing and the signal contribution from the next base T is from pre-phasing.

Phasing correction for this G base call is reflected in the graph on the right side of FIG. 2. As shown for a two-channel sequencer, the fluorescence signal can be represented on a two-dimensional plot, with maximal intensity signal on a "green axis" representing T, maximal intensity on a "red axis" representing C, maximal intensity mid-way between the axes representing A, and minimal intensity on both axes representing G. Without phasing error, the signal for G should have zero intensity on both the red and green axes. Instead, with the phasing error discussed, the fluorescence signal has some intensity contribution on both the green and red axes. In this example, pre-phasing correction reduces the signal intensity to zero on the green axis and phasing correction reduces the signal intensity to zero on the red axis. Similar corrections may be made on base calls for the bases T, C, and A.

Tiles and Flow Cells

Figure 3:
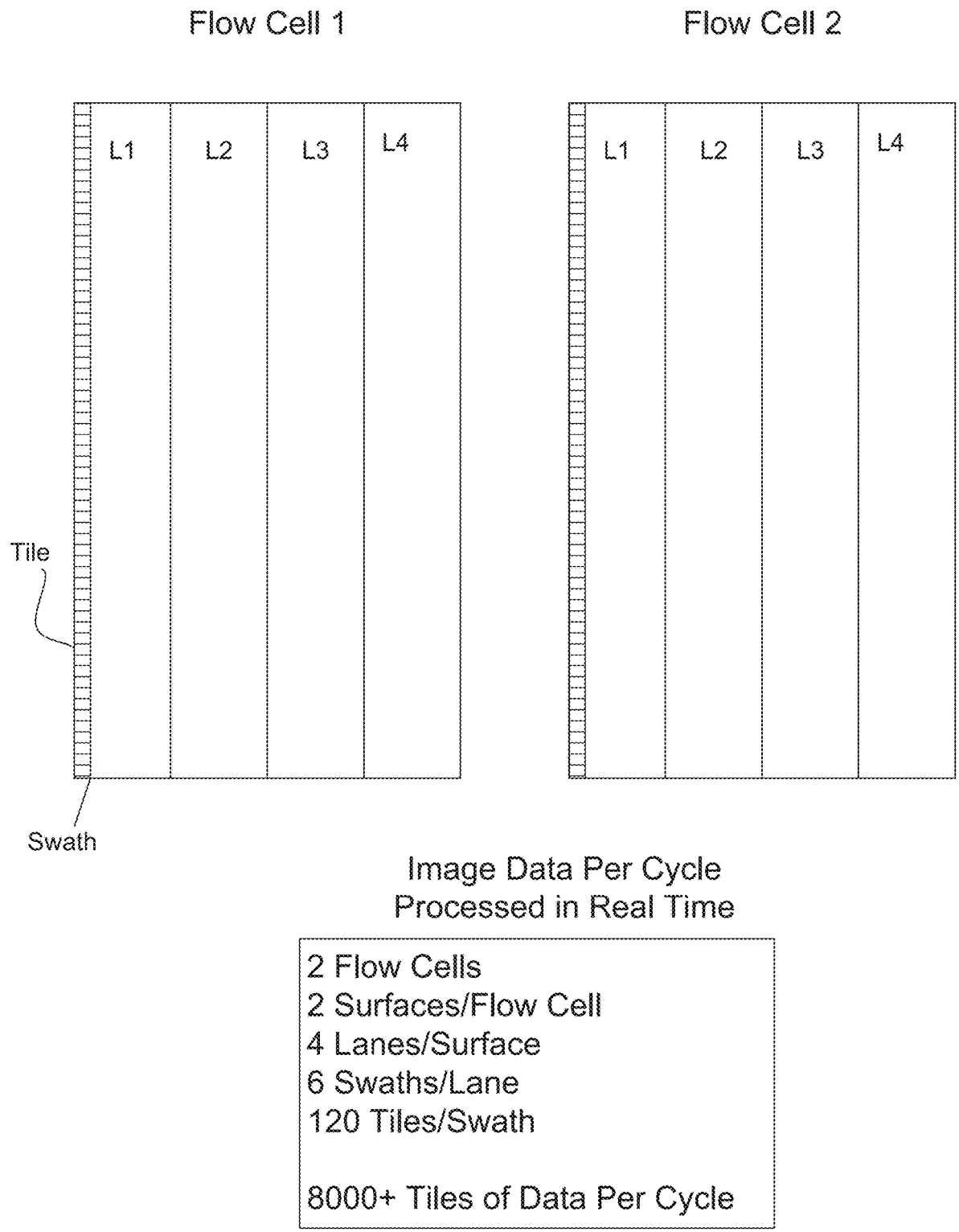
FIG. 3 depicts a flow cell architecture including a plurality of tiles, each containing many clusters.

As explained, a flow cell contains multiple sites where sequencing information is collected. In certain embodiments, each site of a flow cell contains a cluster of single-stranded nucleic acids sharing the same sequence. A single image used in real time sequencing may contain millions of such clusters. A typical flow cell is so large that it requires hundreds or even thousands of separate images to cover its entire area. In certain embodiments, the processor and associated memory employed for real-time analysis processes all these images currently to make base calls for a single cycle. In some implementations, the processor and memory concurrently process all images acquired over two or more flow cells during a single base calling cycle. FIG. 3 schematically depicts a flow cell architecture used in some sequencers from Illumina, Inc. In the depicted example, the sequencer makes concurrent base calls on two flow cells, Flow Cell 1 and Flow Cell 2. In certain embodiments, each flow cell has sequencing sites on each of two surfaces, a top surface in the bottom surface. In such cases, the sequencer images both the top and bottom surfaces during each base calling cycle. As depicted in FIG. 3, each flow cell surface includes four lanes, L1, L2, L3, and L4; of course other numbers are possible. Each lane of each surface may have multiple subdivisions referred to as swaths. Each swath is in turn divided into multiple tiles. For example, there may be approximately 120 tiles per swath. Considering two flow cells, each having two surfaces, with each surface having four lanes, each lane having six swaths, and each swath having 120 tiles, several thousand tiles of data need to be analyzed per cycle. In various embodiments, each tile image (or other image from a portion of a flow cell) is acted on by a single processor thread. In certain embodiments, a sequencer employing a flow cell having the architecture depicted in FIG. 3 processes 8000 or more tiles of data in each base calling cycle. In such cases, the real time processing logic would employ 8000 or more processor threads in each base calling cycle The data from a single tile captured during a single cycle can be stored in the memory as an array, with each entry in the array representing a color value for each channel of a single cluster in the tile. An array for a two-channel arrangement is depicted in FIG. 4. As an example, a color intensity detector can generate signal counts between about 400 and 1500 for each channel. A tile buffer in the system memory is configured to store all the information in the array, in other words the color values of all clusters on a tile at a single base calling cycle. A processor buffer may be similarly configured to store all the information in the array.

Phasing Process

A significant memory burden of real time analysis of sequence data stems from the requirement in phasing correction that two or three cycles of cluster intensities must be saved for every tile for the full length of the run. On an Illumina HiSeqX with a 700 nm flowcell, this takes up 73 Gigabytes of memory. This burden is sufficiently large that most of the data (on this platform) is cached to a solid state hard drive.

Figure 5:
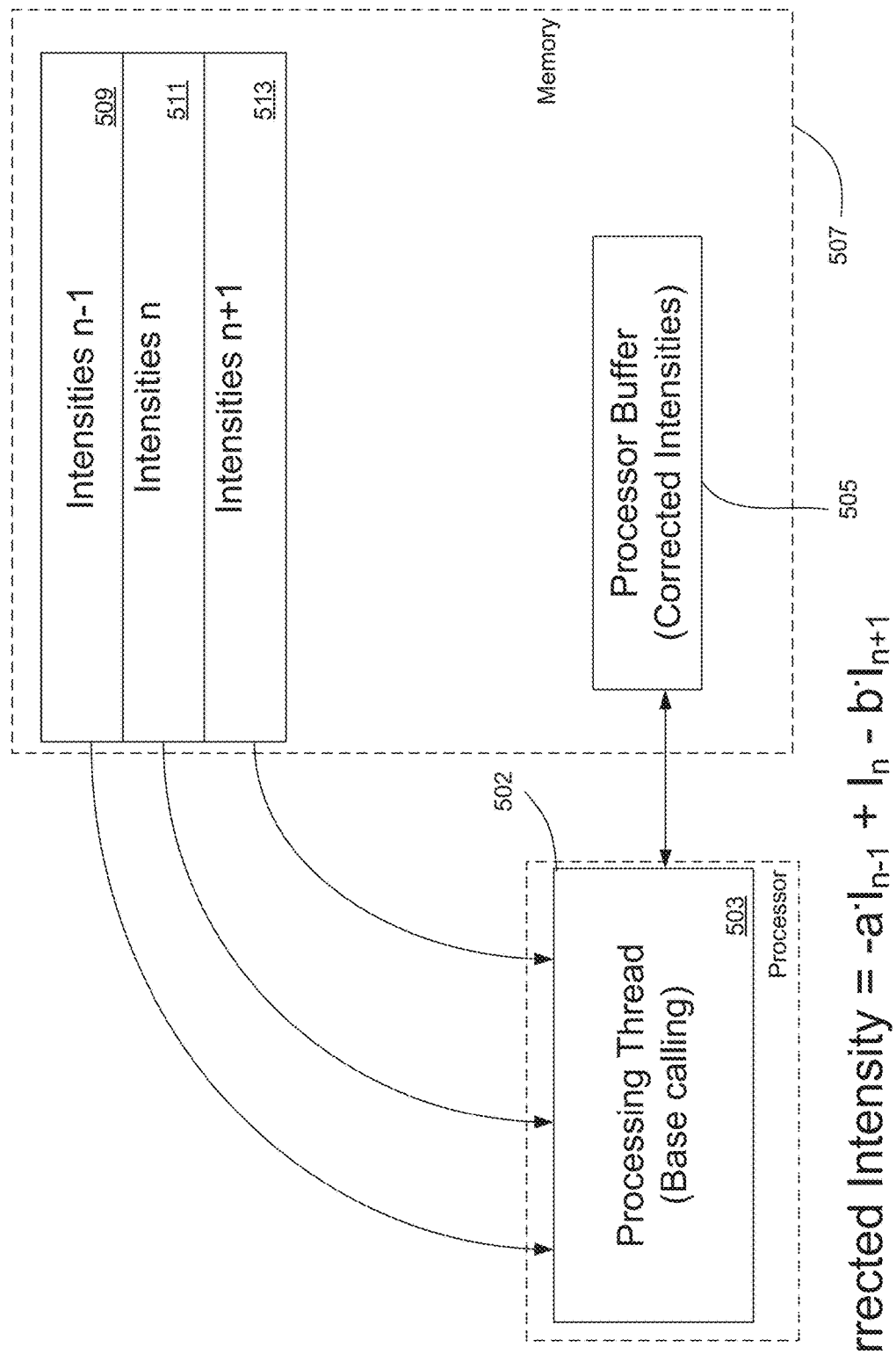
FIG. 5 schematically depicts a first processing configuration and methodology for conducting phasing correction in real time.

As explained, phasing correction adjusts the intensity values of an image to address out of phase sequencing of some nucleic acid stands in a cluster. Phasing correction accomplishes this by starting with the measured cluster color intensity values (or other signals measured by with the sequencing method) for a current base calling cycle and adding or subtracting a correction value using measured intensity values from the previous base calling cycle and/or using measured intensity values from the subsequent base calling cycle. In various implementations, a phasing corrected intensity value for making a base call applies an expression as shown in the bottom of FIG. 5. As shown there, phasing corrected intensity values for a current base calling cycle in an image equal the measured intensity values for the current base calling cycle minus the product of a first coefficient and the measured intensity values at the immediately previous base calling cycle and minus the product of a second coefficient and measured intensity values at the immediately successive base calling cycle:

$$\text{Corrected Intensity} = -a \cdot I_{n-1} + I_n - b \cdot I_{n+1}$$

where $I_{n-1}$, $I_n$, and $I_{n+1}$ are the intensity values of clusters in a tile at the immediately preceding base calling cycle, at the current base calling cycle, and the immediately succeeding base calling cycle respectively. The coefficients a and b are the phasing and pre-phasing coefficients (sometimes called weights), respectively. These may be calculated anew for each base calling cycle of a tile.

Returning to FIG. 2, the measured intensity value for the third base in the depicted sequence (for a single cluster in an image) is shown as dot in the graph on the right side of FIG. 2. The pre-phasing correction to this measured intensity value is reflected by the vertical arrow from the measured intensity value down to the horizontal axis. In the expression for phasing corrected intensity values, this pre-phasing correction is represented by the product of the coefficient b and the intensity value measured for the next successive base calling cycle. In addition, the measured intensity value is corrected by a phasing correction represented by the horizontal arrow on the graph. This phasing correction is implemented by subtracting from the measured intensity value, the product of a coefficient a and the measured intensity value for the immediately preceding base calling cycle. The coefficients a and b may be determined by numerous methods, but in many implementations, they are calculated fresh for each base calling cycle. A description of methods for determining the coefficients to be used in phasing correction is described in International Patent Application having Publication Number WO2015/084985 by Belitz et al. and published on Jun. 11, 2015, which is incorporated herein by reference in its entirety.

In certain embodiments, the phasing algorithm determines phasing coefficients empirically by maximizing the cumulative chastity (or similar metric) of the cluster intensity data during a base calling cycle. One implementation of the algorithm iterates over all or many phasing coefficients and determines which ones give the best results. For example, the phasing algorithm may optimize a and b at every cycle using a pattern search employing a cost function that counts the number of clusters that fail a chastity filter. Thus, a and b are selected to maximize the data quality.

In some embodiments, phasing coefficients are determined as an on-going analysis throughout a sequencing run (e.g., during generate of a read). As a result of this approach, an inaccurate phasing estimation made during early cycles will not adversely affect later cycles.

Some methods determine chastity of a cluster intensity value as a function of relative distances to Gaussian centroids for the other cluster intensity values determined for the same base calling cycle. The centroids ideally align with expected locations of the A, T, C, and G intensities for two channels (see FIG. 2), assuming that a two-channel system is used. In certain embodiments, chastity can be calculated using the expression:

$$\text{chastity} = 1 - D1/(D1 + D2),$$

where D1 is the distance to the nearest Gaussian centroid, and D2 is the distance to the next nearest centroid. Utilizing this approach, when the mean chastity (quality) of intensity values are maximized, the correct values of a and b are chosen. Once these values are identified, then a correction can be applied to all cluster values and base calling can occur directly. Methods of fitting Gaussian distributions to a two-channel data set are described in International Patent Application having Publication Number WO2015/084985, previously incorporated by reference.

In some embodiments, a phasing correction is calculated at nearly every cycle during a sequencing run. In some embodiments, a phasing correction is calculated at every cycle during a sequencing run. In some embodiments, a separate phasing correction is calculated for different locations of an imaged surface at the same cycle. For example, in some embodiments, a separate phasing correction is calculated for every individual lane of an imaged surface, such as an individual flow cell lane. In some embodiments a separate phasing correction is calculated for every subset of a lane, such as an imaging swath within a flow cell lane. In some embodiments, a separate phasing correction is calculated for each individual image, such as, for example, every tile. In certain embodiments, a separate phasing correction is calculated for every tile at every cycle.

As reads get longer, higher order terms can become more important in phasing correction. Thus, in particular embodiments, to correct for this, a second order empirical phasing correction can be calculated. For example, in some embodiments, the method comprises a second order phasing correction as defined by the following:

$$I(cycle)=-a*I(cycle-2)-A*I(cycle-1)+I(cycle)-B*I(cycle+1)-b*I(cycle+2)$$

where I represents intensity and a, A, B, and b represent the first and second order terms to the phasing correction. In particular embodiments, the calculation is optimized over a, A, B, and b.

FIG. 5 schematically depicts a processing configuration and methodology for conducting phasing correction in real time. In the depicted embodiment, a processor 502 creates a new processing thread 503 when the processor is called upon to make base calls from clusters in an image, e.g., an image of a tile. A new thread may be generated for each base calling cycle for each tile. In the depicted embodiment, the processor 502 makes available a single processor buffer 505 for each base calling cycle of a tile (and the designated processing thread). The processor buffer temporarily stores intensity values that are computationally manipulated by the processor to conduct phasing correction for a current base calling cycle n. In the depicted embodiment, the processor interfaces with a system memory 507 containing three buffers, one each for storing image data captured for a particular base calling cycle. In the case of the flow cell architecture depicted in FIG. 3, each buffer stores image data for the clusters of a single tile; hence the buffers are referred to as tile buffers. Of course, for other flow cell architectures and/or image acquisition systems, the buffers may store more or less cluster data. For convenience, the specification will refer to tile buffers. Each tile buffer stores data for a single tile (or other portion of a flow cell) captured during a single base calling cycle. The image data may be provided as an array of data such as shown in FIG. 4.

As depicted, system memory 507 includes a tile buffer 509 which temporarily stores intensity values for the immediately previous base calling cycle (in comparison to the current base calling cycle handled by the processor), a tile buffer 511 which stores intensity values measured for the current base calling cycle, and a tile buffer 513 which stores intensity values for the immediately succeeding base calling cycle. Again, each of the tile buffers 509, 511, and 513 contain measured data of a single tile for a single base calling cycle n.

As shown, thread 503 makes use of the intensity values in each of the tile buffers 509, 511, and 513 during a single base calling cycle. The intensity values are successively loaded into processor buffer 505 and manipulated to implement the phasing correction expression presented at the bottom of FIG. 5. After the base calling process is completed as depicted in the processor and memory configuration of FIG. 5, the processor buffer holds adjusted intensity values used to make a phasing corrected base call.

Figure 6:
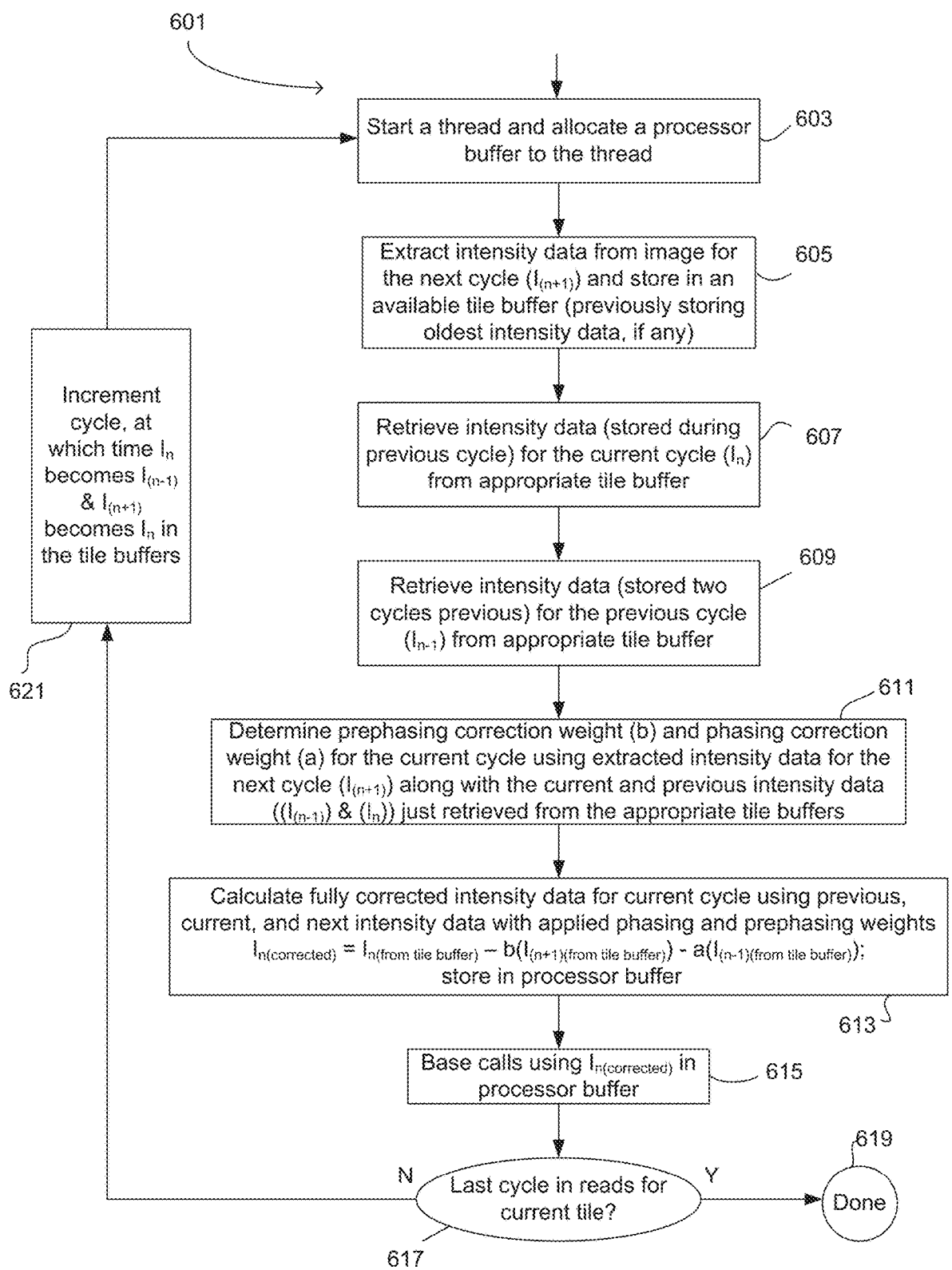
FIG. 6 presents a flowchart of a base calling process that may employ the processor and memory configuration depicted in FIG. 5.

FIG. 6 presents a flowchart of a base calling process that may employ the processor and memory configuration depicted in FIG. 5. As shown in FIG. 6, a process 601 initiates a new base calling cycle by creating a processor thread and allocating a processor buffer to that thread. See process block 603. Thereafter, the processor extracts intensity data from an image of a flow cell tile (or other appropriate portion of the flow cell) taken concurrently with the current processing cycle. In the depicted implementation, the captured image and associated intensity values are the primary intensity values for the next successive base calling cycle, not the current base calling cycle (the current processing iteration). In other words, the current processing cycle performs a base call for image data collected in an immediately preceding processing cycle. Thus, as depicted in a process block 605 of process 601, the extracted intensity values are given the reference $I_{n+1}$, where n represents the current base calling cycle. Stated another way, a processing cycle both (i) calls bases for base calling cycle n, and (ii) captures image data for base calling cycle n+1.

The newly extracted intensity data, which may be provided in the form of an array as depicted in FIG. 4, is stored in an available tile buffer on the system memory (e.g., tile buffer 513). In certain embodiments, this tile buffer is one that stored intensity data that was previously used but is no longer necessary for base calling.

In the current processing cycle, process 601 also retrieves intensity data stored during a computational cycle previous to the current computational cycle. See process block 607. The retrieved intensity data is for the current base calling cycle and is given reference $I_n$. The retrieved intensity data is obtained from an appropriate tile buffer such as tile buffer 511 of the system memory as shown in FIG. 5.

In addition, process 601 retrieves intensity data that was stored two cycles previous to the current base calling cycle. See process block 609. As an example, with reference to FIG. 5, such intensity data may be obtained from a tile buffer 509 of the system memory. The array of intensity values retrieved in operation 609 is identified by $I_{n-1}$.

While operations 605, 607, and 609 are shown as occurring sequentially, this order of operations is flexible and the process can be implemented such that any order is acceptable, so long as it is consistent with base calling that incorporates phasing correction.

Upon retrieving the intensity values for the current base calling cycle (process block 607) and the intensity values for the immediately preceding base calling cycle (processing block 609), the processor has available all intensity values it needs to perform a phasing correction. It does this by first determining the pre-phasing correction weight b and the phasing correction weight a for the current base calling cycle. See process block 611, which illustrates that this may be accomplished using the extracted intensity values for the next succeeding base calling cycle along with the intensity values for the current and immediately preceding base calling cycles. Then, using the phasing and pre-phasing correction weights, the processor calculates phasing corrected intensity values for the current base calling cycle as depicted in process block 613. The corrected values are for the clusters in the tile under consideration. The calculation may employ the expression depicted in block 613. Using the phasing corrected intensity values, the processor makes calls for the current base calling cycle as depicted in process block 615.

At this point, the processing for the current base calling cycle is complete and the next iteration of base calling may be executed. The decision of whether to conduct another base calling cycle is depicted in a block 617 which determines whether there are any further nucleotides to be sequenced in the clusters of the tile under consideration. If there are none, the process is completed as depicted at block 619. If there are, process control is handed to a process block 621 where the processor increments a cycle count. This effectively indexes the intensity values for the current base calling cycle $I_n$ to intensity values for the immediately preceding base calling cycle $I_{n-1}$. At the same time, the intensity values for the immediately next base calling cycle ($I_{n+1}$) become the intensity values for the new current base calling cycle ($I_n$). These increments are made with respect to the indexes applied to the intensity data stored in the tile buffers.

Phasing Process (Reduced Main Memory)

The approach of FIGS. 5 and 6 can work fine so long as the sequencer and its associated real-time analysis system is not memory constrained. However, given the amount of data that must be processed in certain modern sequencers, such as those employed to perform whole genome sequencing, insufficient memory may be available, particularly at a commercially viable cost. Therefore, storing three times the amount of data required to fully image the flow cell (or flow cells) during a base calling cycle can present a serious bottleneck.

A phasing algorithm such as represented in FIGS. 5 and 6 is an important contribution to real time analysis, in that it significantly improves sequencing results, particularly on non-standard samples, e.g. low diversity samples. However, the imposed memory burden becomes greater as the throughput of next generation sequencing systems grows. The following embodiments reduce memory burden by using phasing weights learned from data that was already partially phasing corrected. The phasing and pre-phasing weights can be learned independently and still provide high quality sequencing results. In some examples, the main memory requirement is less than twice the capacity required to store the data contained in the total number of tiles on two flow cells.

Figure 7:
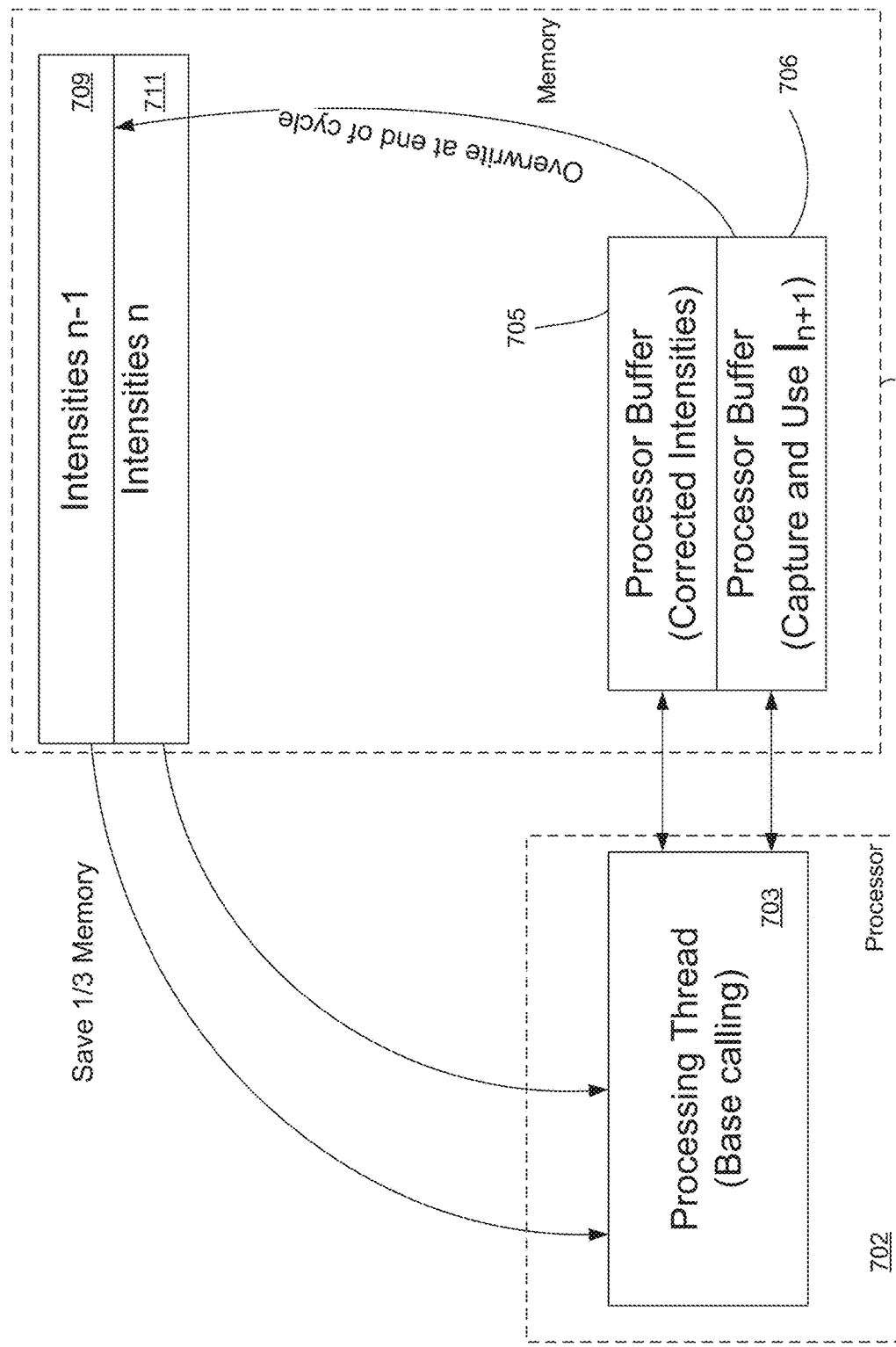
FIG. 7 schematically depicts a second processing configuration and methodology for conducting phasing correction in real time. This configuration reduces the requirements on system memory.

In certain embodiments, the processor and memory configuration for phasing corrected base calling is adjusted to reduce the requirements on system memory. One example of how this works is depicted in FIG. 7. Intensity values are corrected as described above, e.g., phasing and pre-phasing weights are calculated and applied to the immediately preceding and immediately succeeding cycles. However, in the example of FIG. 7, system memory 707 employs only two tile buffers for phasing correction: tile buffer 709 and tile buffer 711. In this example, a processor 702 employs a processing thread 703 which, contrary to the example of FIG. 5, has two associated processor buffers: a processor buffer 705 for storing and operating on the intensity values retrieved from memory 707 and a processor buffer 706 for storing and using the newly captured image intensity values $I_{n+1}$. In the depicted example, the processor buffers are allocated in main memory, but this is not always required. In some embodiments, the processor buffers are allocated in a different physical memory or even on the processor chip.

Replacing tile buffers with processor buffers effectively reduces the total memory requirements. By using multiple processors and/or multithreaded processing, a few processors handle many tiles. As an example, the number of tiles in a system may be on the order of 1000-2000, while the number of processors handling all these tiles is about twenty. In theory, such system can realize a memory reduction on the order of 50×. In some implementations, the reduction is on the order of 20×.

In this implementation, the intensity values captured from tile images in the current processing cycle ($I_{n+1}$) are stored locally on the processor and used to calculate the phasing and pre-phasing weights and subsequently make a base call. In some implementations, only after this process is complete are the most recently captured intensity values ($I_{n+1}$) stored in a tile buffer on system memory 707.

Figure 8:
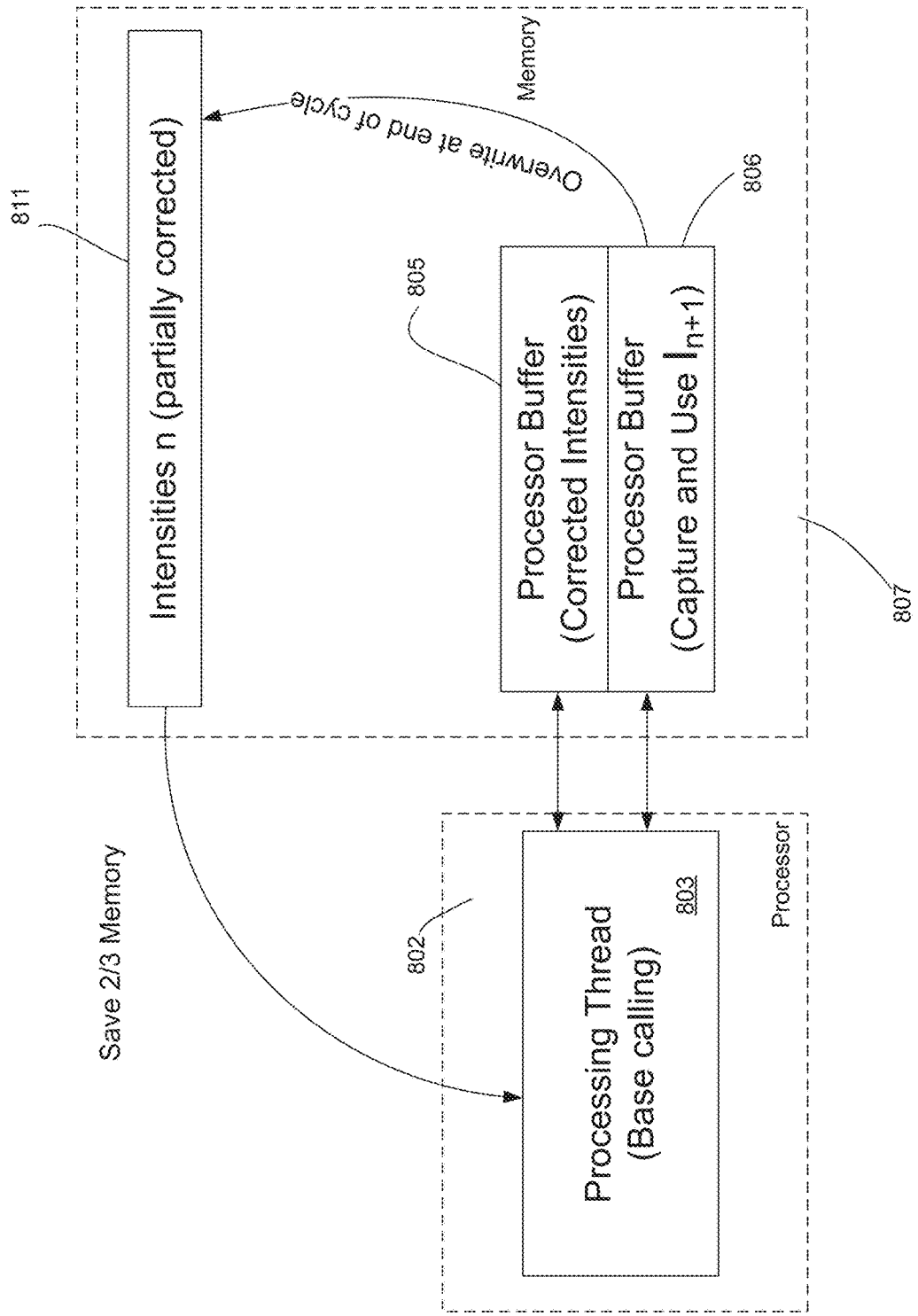
FIG. 8 schematically depicts a third processing configuration and methodology for conducting phasing correction in real time. This configuration further reduces the requirements on system memory.

In some embodiments, a processor and system memory are configured as depicted in FIG. 8. As with the processor/memory configuration in FIG. 7, a processor 802 employs processing threads 803, each associated with two processor buffers: a processor buffer 805 for temporarily storing intensity values from a system memory 807 (tile buffer 811), and a processor buffer 806 for temporarily storing intensity values captured during the current processing cycle ($I_{n+1}$). In order to allow this configuration to work efficiently and effectively, the intensity values stored in tile buffer 811 must be partially phasing corrected. Examples of mechanisms for accomplishing this are described below. Processor buffer 705 in FIG. 7 and processor buffer 805 in FIG. 8 load intensities from main memory and then manipulate those intensities to generate the corrected intensities which are employed for base calling. In the depicted example, the processor buffers are allocated in main memory, but this is not always required. In some embodiments, the processor buffers are allocated in a different physical memory or even on the processor chip.

Figure 9:
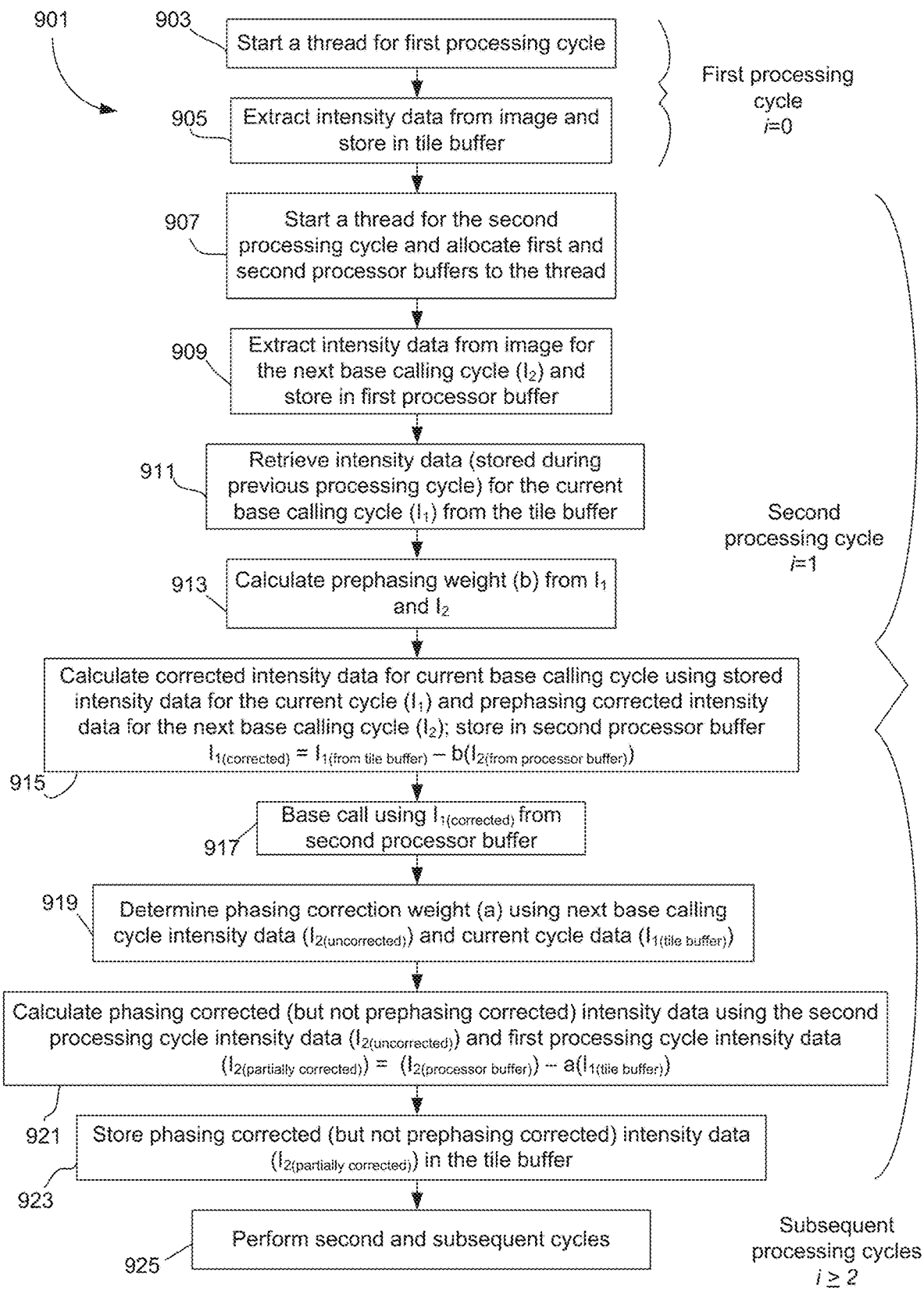
FIG. 9 presents a high-level flowchart of the first few processing cycles that may be employed with the processor and memory configuration of FIG. 8 and, in some implementations, FIG. 7.

FIG. 9 presents a high-level view of a process 901 that may be employed with the processor and memory configuration of FIG. 8 and, in some implementations, FIG. 7. As illustrated in FIG. 9, the first and second processing cycles employ insufficient information to conduct full phasing correction on clusters imaged in a tile. However, phasing is not a significant problem in the very first cycles.

To conduct full phasing correction, the sequencer requires three consecutive cycles of image data. In the first processing cycle, the sequencer does not make a base call; it merely stores intensity data for the next processing, i.e., the cycle in which the first base call is made.

As depicted, the process 901 begins at a process block 903 where a thread is created for the first processing cycle. The instructions in this thread direct extraction of intensity data from an image of the clusters during the first sequencing cycle ($I_1$), i.e. the cycle during which the first nucleotides of the clusters are read. See process block 905. The image data is stored in a tile buffer in system memory. At this point, the first processing cycle is effectively complete.

The process continues at a process block 907 where a new thread is created in preparation for the second processing cycle. In this process, first and second processor buffers are allocated for the second processing cycle. See block 907. Collectively, process blocks 907, 909, 911, 913, 915, 917, 919, 921, and 923 are performed during the second processing cycle, which executes using the thread and processor buffers generated at process block 907.

As depicted, the processor extracts intensity data from the image for the next base calling cycle ($I_2$) and stores that data in a first processor buffer. See process block 909. Next, during the second processing cycle, the processor retrieves the intensity data stored in the tile buffer during the first processing cycle, which intensity data is for the current base calling cycle ($I_1$). See block 911. Using the intensity data collected during the first and second processing cycles, the processor can calculate a pre-phasing weight b for the current base calling cycle (i.e., the first base calls in the reads). See process block 913. With the intensity values for the first two cycles and the pre-phasing weight, the processor calculates corrected intensity data values for the second base calling cycle ($I_2$). The corrected intensity data values may be stored in the second processor buffer. See process block 915. Next, the processor makes the base calls for the second base calling cycle using the corrected intensity data values obtained in block 915. See process block 917.

At this point, the sequencing process is ready to begin preparing for the next base calling cycle. It starts at a process block 919 by determining a phasing correction weight a using the next (or second) base calling cycle intensity data ($I_2$) and the current base calling cycle data ($I_1$), which was stored in the tile buffer. Using the phasing correction weight a, the processor next calculates phasing corrected (but not pre-phasing corrected) intensity data values from the currently uncorrected intensity data ($I_2$) extracted during this second processing cycle and the intensity data values for the first processing cycle ($I_1$) according to the expression presented in process block 921. This results in a partially corrected intensity value array ($I_{2(partially\ corrected)}$) for the second base calling cycle. The sequencer will have to await the next processing cycle before conducting pre-phasing correction. However, at this point much of the calculation is completed and the array data for a single image can be stored in a tile buffer for use in the next base calling cycle. To this end, the processor stores the phasing corrected (but not pre-phasing corrected) intensity data in the tile buffer (such that $I_{2(partially\ corrected)}$ replaces $I_1$ in the tile buffer). See process block 923.

At this point, the first and second processing cycles are completed and base calls are made for the first base calling cycle, which is the second processing cycle. Subsequent base calling cycles may be performed with full phasing correction as described in FIG. 10. See process block 925.

Figure 10:
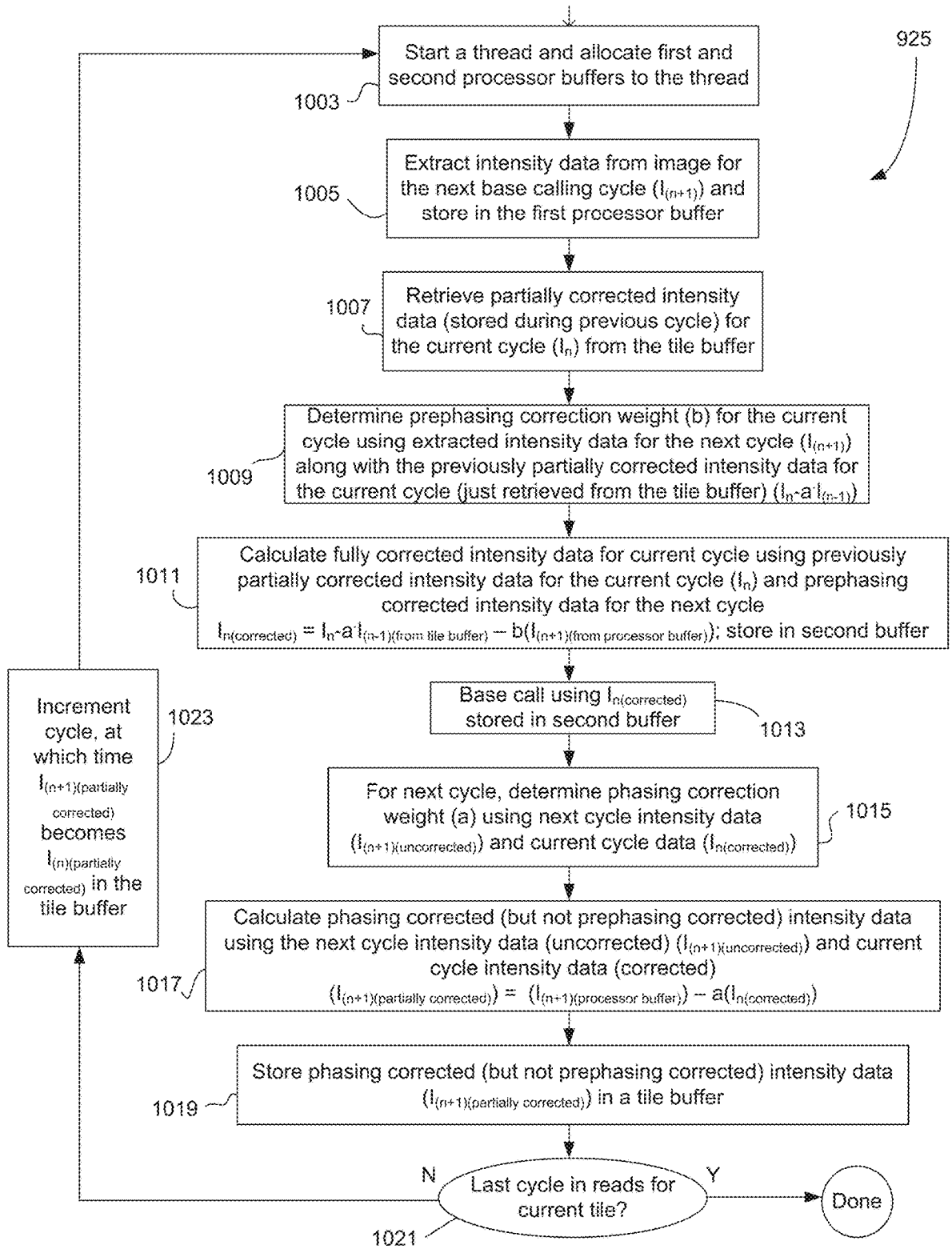
FIG. 10 presents a flow chart of processing cycles that conduct fully phasing corrected base calling. Such cycle may be performed in the third and subsequent processing cycles when sequencing clusters of a tile.

FIG. 10 depicts a sequence of operations it may be performed during a processing cycle that conducts fully phasing corrected base calling. Such cycle may be performed in the third and subsequent processing cycles when sequencing clusters of a tile. In certain embodiments, the sequence of operations depicted in FIG. 10 corresponds to process block 925 of FIG. 9.

As depicted, the process begins by allocating a thread and associated first and second processor buffers. See process block 1003. Next, the processor extracts intensity data values from an image for the next base calling cycle ($I_{n+1}$) and stores those values in a first processor buffer. See process block 1005. Concurrently, the processor retrieves the partially corrected intensity data values that were stored during the previous base calling cycle (as a non-limiting example, $I_{2(partially\ corrected)}$ in the embodiment of FIG. 9, or $I_n-a(I_{n-1})$). These values now represent the intensity values for the current base calling cycle ($I_n$). They were previously stored in the system memory's tile buffer and are now retrieved therefrom. See process block 1007. With the partially corrected intensity data values for the current base calling cycle, which were phasing corrected, the processor need only conduct pre-phasing correction to complete the correction of the intensity data and make the necessary base calls for the current base calling cycle. To this end, the processor determines the pre-phasing correction weight b for the current base calling cycle. It does this using extracted intensity data that it just retrieved from the image data, for the next cycle ($I_{n+1}$), along with the previously partially corrected intensity data for the current base calling cycle. Recall that this partially corrected data that was just retrieved from the tile buffer. The partially corrected intensity data may be represented by the expression $I_n-a(I_{n-1})$. See process block 1009.

With the pre-phasing correction weight b calculated for the current base calling cycle, the processor has all it needs to calculate a fully phasing corrected intensity data array for the current base calling cycle ($I_n$). The calculation is conducted as depicted in process block 1009. The resulting fully corrected intensity data values are stored in the second processor buffer. See process block 1011. Thereafter, the processor makes the base calls for the current base calling cycle using the corrected intensity data values stored in the second processor buffer. See process block 1013.

The current processing cycle can begin preparing for the next base calling cycle which will be executed during the next processing cycle. In the depicted embodiment, the processor determines the phasing correction weight a for the next base calling cycle using intensity data available for the current base calling cycle. See process block 1015. Recall that the next base calling cycle intensity data was extracted and stored in the first processor buffer at process operation 1005. Partially corrected intensity values for the current base calling cycle were retrieved from the tile buffer for purposes of making the current base calls. The same partially corrected intensity values are now used to calculate the phasing correction weight a for the next base calling cycle. With the phasing correction weight for the next base calling cycle now calculated, the processor calculates phasing corrected (but not pre-phasing corrected) intensity data values as depicted in process block 1017. Processor then stores these phasing corrected intensity data values for the next base calling cycle in the tile buffer. See process block 1019.

Before this invention, it was assumed that that base calling accuracy would suffer by learning prephasing weights from phasing corrected intensities. However, the results herein show that little or no inaccuracy results. In some implementations, the image data is compressed (e.g., lossy compression) and even the partially phase corrected data is compressed. In both cases, it has been demonstrated that the compression could be performed without loss of accuracy. As an example, without compression, an implementation uses two float buffers for each tile (a float buffer is 4 bytes in size). With compression, an implementation uses a single byte buffer, thus realizing 4× less memory.

At this point the current processing cycle is effectively complete, so the processor determines whether there are any more cycles that need be conducted in sequencing the clusters of the current tile. See decision block 1021. If no further bases need be read from the clusters, the process is complete and no further processing cycles are conducted. However, if one or more additional sequencing cycles are required, process control is directed to a process block 1023 where the processor increments the current cycle at which point the partially corrected intensity data values stored in the tile buffer become current; i.e., they become the values for the new base calling cycle. Process control then returns to process block 1003 where the next processing cycle begins.

EXAMPLE

As explained, certain embodiments reduce memory burden by using phasing weights learned from data that was already partially phasing corrected. However, it was not clear that the phasing and pre-phasing weights can be learned independently and still provide high quality sequencing results. The example presented in FIG. 11 establishes that they can.

As shown, two comparisons were made, each using a baseline process (e.g., a process of FIGS. 5 and 6) and a new process that was optimized to reduce main memory requirements (e.g., a process of FIGS. 8 and 10). In each comparison, the same sequencer and sample were employed. Specifically, an Illumina HiSeqX instrument was converted to use 2 dye chemistry. The sequencer's output images were saved and the two phasing algorithms were both tested on the same sequencing images, providing a completely controlled test. The "Clusters PF" indicates the throughput delivered by the sequencer; the % Aligned indicates the number of clusters that successfully aligned to the reference genome, and the "% Error Rate" indicates the mean error rate of the sequences called by the software compared to the reference genome.

The sequencing results demonstrate that the memory-efficient phasing algorithm is comparable to the baseline algorithm. In this example, the memory efficient process produced an approximately 3% increase in error rate, which is offset by a reduction in main memory (estimated be from 420 Gigabytes to 340 Gigabytes in some implementations).

Sequencing Methods

As indicated above, the disclosure pertains to sequencing nucleic acid samples. Any of a number of sequencing technologies using one or more channels of information for base calling, particularly optical channels, may be used. Particularly applicable techniques are those where nucleic acids are attached at fixed locations in an array (e.g., as cluster) and where the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Certain embodiments include sequencing-by-synthesis ("SBS") techniques. While sequencing by synthesis techniques are emphasized here, other sequencing technologies may be employed.

In many implementations, SBS techniques involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.]

In another exemplary type of SBS, cycle sequencing is accomplished by stepwise addition of reversible terminator nucleotides containing, for example, a cleavable or photo-bleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In reversible terminator-based sequencing embodiments, the labels may not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope"

Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

The methods set forth herein can provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some cases, single-end reads of greater than 500 bp are employed for reads of greater than about 1000 bp when paired end reads are generated. Mapping of the sequence tags is achieved by comparing the sequence of the tag with the sequence of the reference to determine the chromosomal origin of the sequenced nucleic acid molecule, and specific genetic sequence information is not needed. A small degree of mismatch (0-2 mismatches per sequence tag) may be allowed to account for minor polymorphisms that may exist between the reference genome and the genomes in the mixed sample.

Systems and Apparatus for Real Time Analysis of Sequencing Data

Analysis of the sequencing data is typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads derived from a nucleic acid sample, counts or densities of such tags that align with particular regions of a reference sequence (e.g., that align to a chromosome or chromosome segment), separation distances between adjacent reads or fragments, distributions of such separation distances, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for determining phasing and pre-phasing coefficients, as well as phasing corrected magnitude values and associated base calls. The computer product may contain instructions for performing any one or more of the above-described methods for phasing and base calling. As explained, the computer product may include a non-transitory and/or tangible computer readable medium having a computer executable or compilable logic (e.g., instructions) recorded thereon for enabling a processor to align reads, identify fragments and/or islands from aligned reads, identify alleles, including indel alleles, of heterozygous polymorphisms, phase portions of chromosomes, and haplotype chromosomes and genomes. In one example, the computer product includes (1) a computer readable medium having a computer executable or compilable logic (e.g., instructions) stored thereon for enabling a processor conduct phasing correction on magnitude data (e.g., color intensity data from two or more channels) on nucleic acid samples; (2) computer assisted logic for making base calls of the nucleic acid samples; and (3) an output procedure for generating an output characterizing the nucleic acid samples.

It should be understood that it is not practical, or even possible in most cases, for an unaided human being to perform the computational operations of the methods disclosed herein. For example, generating phasing coefficients for even a single tile during a single base calling cycle might require years of effort without the assistance of a computational apparatus. Of course, the problem is compounded because reliable NGS sequencing generally require phasing correction and base calling for at least thousands or even millions of reads.

The methods disclosed herein can be performed using a system for sequencing nucleic acid samples. The system may include: (a) a sequencer for receiving nucleic acids from the test sample providing nucleic acid sequence information from the sample; (b) a processor; and (c) one or more computer-readable storage media having stored thereon instructions for execution on the processor to evaluate data from the sequencer. The computer-readable storage media may also store partially phasing corrected magnitude data from the clusters on a flow cell.

In some embodiments, the methods are instructed by a computer-readable medium having stored thereon computer-readable instructions for carrying out a method for determining the phase of a sequence. Thus one embodiment provides a computer program product include one or more computer-readable non-transitory storage media having stored thereon computer-executable instructions that, when executed by one or more processors of a computer system, cause the computer system to implement a method for sequencing a DNA sample. The method includes: (a) obtain data representing an image (e.g., the image itself) of a substrate comprising a plurality of sites where nucleic acid bases are read; (b) obtain color values (or other values representing individual bases/nucleotides) of the plurality of sites from the image of the substrate; (c) store the color values in a processor buffer; (d) retrieve partially phase-corrected color values of the plurality of sites for a base calling cycle, where the partially phase-corrected color values were stored in the sequencer's memory during an immediately preceding base calling cycle; (e) determine a prephasing correction from (i) the partially phase-corrected color values stored during the immediately preceding base calling cycle, and (ii) the color values stored in the processor buffer; and (f) determine corrected color values from (i) the color values in the processor buffer, (ii) the partially phase corrected values stored during the immediately preceding cycle, and (iii) the prephasing correction.

Sequence or other data can be input into a computer or stored on a computer readable medium either directly or indirectly. In various embodiments, a computer system is on board or directly coupled to a sequencing device that reads and/or analyzes sequences of nucleic acids from samples. Sequences or other information from such tools are provided to the computer system (or simply on board processing hardware) via a data transmission interface. In addition, the memory device may store reads, base calling quality information, phasing coefficients information, etc. The memory may also store various routines and/or programs for analyzing and presenting the sequence data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. For example, reads may be transmitted as they are generated, or soon thereafter, and aligned and other analyzed remotely. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads) and sending the data to a computer or other computational system. For example, the computer can be connected to laboratory equipment, e.g., a sample collection apparatus, a polynucleotide amplification apparatus, or a nucleotide sequencing apparatus. The data collected or stored can be transmitted from the computer to a remote location, e.g., via a local network or a wide area network such as the internet. At the remote location various operations can be performed on the transmitted data.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform single molecule sequencing.

CONCLUSION

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method of determining corrected color values from image data acquired, during a base calling cycle, by a nucleic acid sequencer comprising an image acquisition system, one or more processors, and memory, the method comprising:
    (a) obtaining an image of a substrate comprising a plurality of sites where nucleic acid bases are read, wherein the sites exhibit colors representing nucleic acid base types;
    (b) measuring color values of the plurality of sites from the image of the substrate;
    (c) storing the color values in a processor buffer of the sequencer's one or more processors;
    (d) retrieving partially phase-corrected color values of the plurality of sites, wherein the partially phase-corrected color values were stored in the sequencer's memory during an immediately preceding base calling cycle;
    (e) determining a prephasing correction from
        the partially phase-corrected color values stored during the immediately preceding base calling cycle, and
        the color values stored in the processor buffer; and
    (f) determining the corrected color values from
        the color values in the processor buffer,
        the partially phase corrected values stored during the immediately preceding cycle, and
        the prephasing correction.

2. The method of claim 1, further comprising using the corrected color values to make base calls for the plurality of sites.

3. The method of claim 1, further comprising determining a phasing correction for the immediately succeeding base calling cycle.

4. The method of claim 3, wherein determining the phasing correction for the immediately succeeding base calling cycle comprises analyzing
    the partially phase-corrected color values stored in the sequencer's memory, and
    the color values stored in the processor buffer.

5. The method of claim 3, further comprising:
    producing partially phase-corrected color values for the immediately succeeding base calling cycle by applying the phasing correction to color values of the plurality of sites stored in the sequencer's memory; and
    storing the partially phase-corrected color values for the immediately succeeding base calling cycle in the sequencer's memory.

6. The method of claim 1, wherein the method is performed in real time during acquisition of sequence reads by the nucleic acid sequencer.

7. The method of claim 1, wherein the color values are determined from only two channels of the sequencer.

8. The method of claim 1, wherein the substrate comprises a flow cell, wherein the flow cell is logically divided into tiles, and wherein each tile represents a region of the flow cell comprising a subset of sites, which subset is captured in a single image from the image acquisition system.

9. The method of claim 8, wherein, in operation (d), the partially phase-corrected color values were stored in tile buffers of the sequencer's memory, and wherein the tile buffers are designated for storing data representing images of individual tiles on the substrate.

10. The method of claim 8, further comprising, prior to operation (a), providing reagents to the flow cell and allowing the reagents to interact with sites to exhibit the colors representing nucleic acid base types during the base calling cycle.

11. The method of claim 1, further comprising allocating the processor buffer and a second processor buffer, wherein the second processor buffer is used to determine the corrected color values in (f).

12. A nucleic acid sequencer comprising:
an image acquisition system;
memory; and
one or more processors designed or configured to:
(a) obtain data representing an image of a substrate comprising a plurality of sites where nucleic acid bases are read, wherein the sites exhibit colors representing nucleic acid base types;
(b) obtain color values of the plurality of sites from the image of the substrate;
(c) store the color values in a processor buffer;
(d) retrieve partially phase-corrected color values of the plurality of sites for a base calling cycle, wherein the partially phase-corrected color values were stored in the memory during an immediately preceding base calling cycle;
(e) determine a prephasing correction from
the partially phase-corrected color values stored during the immediately preceding base calling cycle, and
the color values stored in the processor buffer; and
(f) determine corrected color values from
the color values in the processor buffer,
the partially phase corrected values stored during the immediately preceding cycle, and
the prephasing correction.

13. The nucleic acid sequencer of claim 12, wherein the one or more processors an further designed or configured to use the corrected color values to make base calls for the plurality of sites.

14. The nucleic acid sequencer of claim 12, wherein the one or more processors are further designed or configured to determine a phasing correction for an immediately succeeding base calling cycle.

15. The nucleic acid sequencer of claim 14, wherein the one or more processors are designed or configured to determine the phasing correction for the immediately succeeding base calling cycle by analyzing
the partially phase-corrected color values stored in the memory, and
the color values stored in the processor buffer.

16. The nucleic acid sequencer of claim 14, wherein the one or more processors are further designed or configured to:
produce partially phase-corrected color values for the immediately succeeding base calling cycle by applying the phasing correction to color values of the plurality of sites stored in the memory; and
store the partially phase-corrected color values for the immediately succeeding base calling cycle in the memory.

17. The nucleic acid sequencer of claim 12, wherein the one or more processors are designed or configured to perform (a)-(f) in real time during base calling.

18. The nucleic acid sequencer of claim 12, wherein the one or more processors are designed or configured to obtain the color values from only two channels.

19. The nucleic acid sequencer of claim 12, wherein the substrate comprises a flow cell, wherein the flow cell is logically divided into tiles, and wherein each tile represents a region of the flow cell comprising a subset of sites, which subset is captured in a single image from the image acquisition system.

20. The nucleic acid sequencer of claim 19, wherein the one or more processors are further designed or configured to, prior to operation (a), provide reagents to the flow cell and allow the reagents to interact with sites to exhibit the colors representing nucleic acid base types during the base calling cycle.

21. The nucleic acid sequencer of claim 20, wherein the one or more processors are further designed or configured to, after operation (f):
provide fresh reagents to the flow cell and allow the fresh reagents to interact with the sites to exhibit colors representing nucleic acid base types for a next base calling cycle; and
repeat operations (a)-(e) for the next base calling cycle.

22. The nucleic acid sequencer of claim 12, wherein the one or more processors are further designed or configured to allocate the processor buffer and a second processor buffer for determining the corrected color values in (f).

* * * * *